United States Patent [19]

McCarthy et al.

[11] Patent Number: 5,120,764
[45] Date of Patent: Jun. 9, 1992

[54] INHIBITORS OF LYSYL OXIDASE

[75] Inventors: James R. McCarthy, West Chester; Charlotte L. Barney, Cincinnati; Donald P. Matthews, West Chester; Philippe Bey, Cincinnati, all of Ohio

[73] Assignee: Merrell Dow Pharmaceuticals Inc., Cincinnati, Ohio

[21] Appl. No.: 265,654

[22] Filed: Nov. 1, 1988

[51] Int. Cl.⁵ .......................................... A61K 31/195
[52] U.S. Cl. .................................................. 514/562
[58] Field of Search ......................................... 514/562

[56] References Cited

U.S. PATENT DOCUMENTS

| 4,454,158 | 6/1984 | Bey | 514/562 |
| 4,650,907 | 3/1987 | Bey et al. | 514/562 |
| 4,847,288 | 7/1989 | McCarthy | 514/438 |

FOREIGN PATENT DOCUMENTS 2162518  2/1986  United Kingdom .

OTHER PUBLICATIONS

C. Sahlberg et al., *J. Med. Chem.*, vol. 26, No. 7, pp. 1036–1042 (1983).
A. Claesson et al., *Tetrahedron Letters* vol. 18, No. 3, pp. 363–368 (1982).
J. R. McCarthy et al., *Tetrahedron Letters* vol. 28, No. 20, pp. 2207–2210 (1987).

*Primary Examiner*—Robert Gerstl
*Attorney, Agent, or Firm*—Michael J. Sayles; Stephen L. Nesbitt

[57] ABSTRACT

This invention relates to certain inhibitors of lysyl oxidase and their use in the treatment of diseases and conditions associated with the abnormal deposition of collagen.

2 Claims, No Drawings

INHIBITORS OF LYSYL OXIDASE

Collagen is the main protein of skin, tendon, bone, cartilage, and connective tissue. Collagen molecules are characterized by a triple-stranded helical structure made up of α-chains, and each collagen molecule is about 300 nm long and about 1.5 nm in diameter. Precursor pro-α-chains having certain residues called extension peptides not present in the final product, are the initial products of RNA mediated peptide synthesis within fibroblasts. These pro-α-chains first assemble into triple-stranded procollagen molecules intracellularly and the component lysine and proline residues are hydroxylated and subsequently glycosylated. During secretion, the extension peptides of the procollagen molecules are cleaved and collagen is formed. After secretion, collagen assembles into microfibrils and ultimately fibrils.

Strength of collagen is provided by crosslinking between various lysine residues both within a fibril and between fibrils. The first step of the crosslinking process is the deamination of lysine and hydroxylysine residues by extracellular lysyl oxidase to produce aldehyde groups. These highly reactive groups then form the crosslinks. The amount and type of crosslinking varies greatly according to the strength requirements of the various tissue types. If crosslinking is inhibited, the tissue becomes fragile and accordingly tears quite easily. Certain serious medical conditions are associated with the lack of collagen crosslinking such as Ehlers-Danlos Syndrome and Marfan's syndrome. While collagen crosslinking is essential, in certain instances it is desirable to prevent or reduce crosslinking such as in conditions and diseases characterized by defects in collagen metabolism such as occurs in various fibrotic conditions, for example, lung fibrosis, as well as in proliferative vitreo retinopathy, surgical scarring, systemic sclerosis, scleroderma, and keloids.

Certain inhibitors of collagen crosslinking are known such as penicillamine and beta-aminopropionitrile (BAPN). BAPN is known to prevent crosslinking specifically because of its ability to inhibit lysyl oxidase. Both penicillamine and BAPN have been studied extensively in animals and in humans for their effects on conditions associated with the abnormal deposition of collagen. The applicants have now discovered that certain allenyl amines are inhibitors of lysyl oxidase and are useful in the treatment of diseases and conditions associated with abnormal collagen deposition.

SUMMARY OF THE INVENTION

Compounds of formula 1

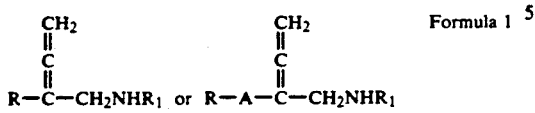

Formula 1 wherein
$R_1$ is a hydrogen, or a $(C_1-C_4)$alkyl group;
A is a divalent radical group selected from

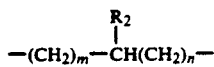

wherein $R_2$ is hydrogen, methyl, or ethyl, and m and n, independently, are an integer from 0 to 16, provided that $m+n$ cannot be greater than 17;

$$-(CH_2)_p-D-(CH_2)_q-$$

wherein
D is oxygen or sulfur, p is an integer of from 0 to 16, and q is an integer of from 1 to 16, provided that $m+n$ cannot be greater than 17; and $$-(CH_2)_r-CH=CH-(CH_2)_s-$$

wherein
s is an integer of from 1 to 16 and r is an integer of from 0 to 16, provided that $r+s$ cannot be greater than 16; and R is a methyl group, a $(C_3-C_8)$cycloalkyl group, a phenyl, or a phenyl substituted with one or two members of the group $(C_1-C_5)$alkyl, $(C_1-C_5)$alkoxy, hydroxy, chloro, bromo, fluoro, iodo, trifluoromethyl, nitro, $(C_1-C_5)$alkylcarbonyl, benzoyl, or phenyl; or R is 1- or 2-naphthyl; 1-, 2-, or 3-indenyl; 1-, 2-, or 9-fluorenyl; 1-, 2-, or 3-piperidinyl; 2- or 3-pyrrolyl; 2- or 3-thienyl; 2- or 3-furanyl; 2- or 3-indolyl; 2- or 3-thianaphthylenyl; or 2- or 3-benzofuranyl; or wherein A is a divalent radical group selected from

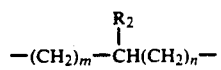

wherein m, n and $R_2$ are as defined above, then R can additionally be a $-NH_2$ group; or a pharmaceutically acceptable salt thereof are inhibitors of lysyl oxidase and are therefore useful in the treatment of various diseases and conditions characterized by abnormal collagen deposition.

DETAILED DESCRIPTION OF THE INVENTION

Illustrative examples of divalent groups represented by A are $-CH_2-$, $-(CH_2)_2-$, $-(CH_2)_3-$, $-(CH_2)_4-$, $-(CH_2)_5-$, $-CH_2-(CH_2)_2-$, $-CH_2O(CH_2)_2-$, and $-CH=CH-CH_2-$. The term "$(C_1-C_5)$alkyl" means straight- and branched-chain alkyl groups. Illustrative examples of $(C_1-C_5)$alkyl groups are methyl, ethyl, n-propyl, isopropyl, n-butyl, isobutyl, tert-butyl, and n-pentyl. Illustrative examples of $(C_3C_8)$cycloalkyl groups are cyclopropyl, cyclobutyl, cyclopentyl, cyclohexyl, cycloheptyl, and cyclooctyl. The term "$(C_1-C_5)$alkoxy" means straight- and branched-chain alkoxy groups. Illustrative examples of $(C_1-C_5)$alkoxy are methoxy, ethoxy, n-propoxy, isopropoxy, n-butoxy, isobutoxy, and n-pentoxy. The term "$(C_1-C_5)$alkylcarbonyl" means both straight- and branched-chain alkylcarbonyl groups. Examples of such groups are acetyl, propionyl, and n-butyryl.

It will be apparent to those skilled in the art that certain compounds of Formula 1 contain a carbon-carbon double bond, and therefore geometric isomerism is possible. In naming the compounds of this invention the prefixes "(E)" and "(Z)" are used in the conventional manner to indicate stereochemistry at the double bonds. If no stereochemical designation is given, both the substantially pure isomers or mixtures are intended.

The compounds of this invention are useful both in the free base form and in the form of acid addition salts.

The acid addition salts are simply a more convenient form for use and, in practice, use of the salt amounts to use of the free base. The expression "pharmaceutically acceptable acid addition salts" is intended to apply to any non-toxic organic or inorganic acid addition salts of the base compounds of formula 1. Illustrative inorganic acids which form suitable salts include hydrochloric, hydrobromic, sulfuric, and phosphoric acids and acid metal salts such as sodium monohydrogen orthophosphate and potassium hydrogen sulfate. Illustrative organic acids which form suitable salts include the mono, di, and tricarboxylic acids. Illustrative of such acids are, for example, acetic, glycolic, lactic, pyruvic, malonic, succinic, glutaric, fumaric, malic, tartaric, citric, ascorbic, maleic, hydroxymaleic, benzoic, hydroxybenzoic, phenylacetic, cinnamic, salicylic, and 2-phenoxybenzoic acids. Other organic acids which form suitable salts are the sulfonic acids such as methane sulfonic acid and 2-hydroxyethane sulfonic acid. The salts can exist in either a hydrated or a substantially anhydrous form. The acid salts are prepared by standard techniques such as by dissolving the free base in aqueous or aqueous-alcohol solution or other suitable solvent containing the appropriate acid and isolating by evaporating the solution, or by reacting the free base in an organic solvent in which case the salt separates directly or can be obtained by concentration of the solution. In general the acid addition salts of the compounds of this invention are crystalline materials which are soluble in water and various hydrophilic organic solvents and which in comparison to their free base forms, demonstrate higher melting points and an increased solubility.

Illustrative examples of the compounds of formula 1 are:
2-isobutyl-2,3-butadienylamine;
2-isopropyl-2,3-butadienylamine;
2-(9-octadecenyl)-2,3-butadienylamine;
2-(3-methyl-3-butenyl)-2,3-butadienylamine;
2-(4-methoxy-2-butenyl)-2,3-butadienylamine;
2-sec-butyl-2,3-butadienylamine;
2-butyl-2,3-butadienylamine;
2-hexyl-2,3-butadienylamine;
2-heptyl-2,3-butadienylamine;
2-ethoxymethyl-2,3-butadienylamine;
2-thioethoxymethyl-2,3-butadienylamine;
2-phenyl-2,3-butadienylamine;
2-(2-methoxyphenyl)-2,3-butadienylamine;
2-(3-methoxyphenyl)-2,3-butadienylamine;
2-(4-methoxyphenyl)-2,3-butadienylamine;
2-(2,3-dimethoxyphenyl)-2,3-butadienylamine;
2-(2,4-dimethoxyphenyl)-2,3-butadienylamine;
2-(2,5-dimethoxyphenyl)-2,3-butadienylamine;
2-(2,6-dimethoxyphenyl)-2,3-butadienylamine;
2-(3,4-dimethoxyphenyl)-2,3-butadienylamine;
2-(3,5-dimethoxyphenyl)-2,3-butadienylamine;
2-(2-hydroxyphenyl)-2,3-butadienylamine;
2-(3-hydroxyphenyl)-2,3-butadienylamine;
2-(4-hydroxyphenyl)-2,3-butadienylamine;
2-(2,3-dihydroxyphenyl)-2,3-butadienylamine;
2-(2,4-dihydroxyphenyl)-2,3-butadienylamine;
2-(2,5-dihydroxyphenyl)-2,3-butadienylamine;
2-(2,6-dihydroxyphenyl)-2,3-butadienylamine;
2-(3,4-dihydroxyphenyl)-2,3-butadienylamine;
2-(3,5-dihydroxyphenyl)-2,3-butadienylamine;
2-benzyl-2,3-butadienylamine;
2-phenethyl-2,3-butadienylamine;
2-(2-methoxybenzyl)-2,3-butadienylamine;
2-(3-methoxybenzyl)-2,3-butadienylamine;
2-(4-methoxybenzyl)-2,3-butadienylamine;
2-(2,3-dimethoxybenzyl)-2,3-butadienylamine;
2-(2,4-dimethoxybenzyl)-2,3-butadienylamine;
2-(2,5-dimethoxybenzyl)-2,3-butadienylamine;
2-(2,6-dimethoxybenzyl)-2,3-butadienylamine;
2-(3,4-dimethoxybenzyl)-2,3-butadienylamine;
2-(3,5-dimethoxybenzyl)-2,3-butadienylamine;
2-(2-hydroxybenzyl)-2,3-butadienylamine;
2-(3-hydroxybenzyl)-2,3-butadienylamine;
2-(4-hydroxybenzyl)-2,3-butadienylamine;
2-(2,3-dihydroxybenzyl)-2,3-butadienylamine;
2-(2,4-dihydroxybenzyl)-2,3-butadienylamine;
2-(2,5-dihydroxybenzyl)-2,3-butadienylamine;
2-(2,6-dihydroxybenzyl)-2,3-butadienylamine;
2-(3,4-dihydroxybenzyl)-2,3-butadienylamine;
2-(3,5-dihydroxybenzl)-2,3-butadienylamine;
2-phenoxymethyl-2,3-butadienylamine;
2-(4-methoxyphenoxymethyl)-2,3-butadienylamine;
2-(2,4-dimethoxyphenoxymethyl)-2,3-butadienylamine;
2-(2,6-dimethoxyphenoxymethyl)-2,3-butadienylamine;
2-(3,4-methylenedioxyphenoxymethyl)-2,3-butadienylamine;
2-(3-hydroxyphenoxymethyl)-2,3-butadienylamine;
2-(4-hydroxyphenoxymethyl)-2,3-butadienylamine;
2-(2,3-dihydroxyphenoxymethyl)-2,3-butadienylamine;
2-(2,4-dihydroxyphenoxymethyl)-2,3-butadienylamine;
2-(2-methylphenoxymethyl)-2,3-butadienylamine;
2-(2-chlorophenoxymethyl)-2,3-butadienylamine;
2-(4-chlorophenoxymethyl)-2,3-butadienylamine;
2-(4-trifluoromethylphenoxymethyl)-2,3-butadienylamine;
2-thiophenoxymethyl-2,3-butadienylamine;
2-(4-methoxythiophenoxymethyl)-2,3-butadienylamine;
2-(2,4-dimethoxythiophenoxymethyl)-2,3-butadienylamine;
2-(2,4-dichlorothiophenoxymethyl)-2,3-butadienylamine;
2-(4-hydroxythiophenoxymethyl)-2,3-butadienylamine;
2-(1-naphthyloxymethyl)-2,3-butadienylamine;
2-(2-naphthyloxymethyl)-2,3-butadienylamine; and
2-aminomethyl-2,3-butadienylamine.

As with any group of structurally-related active molecules, certain species are preferred. In this instance, applicants prefer those compounds of formula 1 wherein $R_1$ is hydrogen as well as those compounds wherein R is a phenyl group optionally substituted with ($C_1$–$C_5$)alkyl, ($C_1$–$C_5$)alkoxy, hydroxy, chloro, fluoro, bromo, or iodo, or wherein R is a 2- or 3-thienyl, 2- or 3-thianaphthenyl or 2- or 3-benzofuraryl group or wherein R is a methyl group or a ($C_3$–$C_8$)cycloalkyl group.

More preferred are those compounds of formula 1 wherein A is not present or is a methylene or ethylene group, particularly those compounds wherein R is a phenyl group optionally substituted with a chloro, fluoro, methyl, methoxy, or hydroxy group, as well as those compounds wherein R is a 2-thianaphthenyl or 2-benzofuraryl group, a thienyl group or a cyclopentyl group. Also more preferred are those formula 1 compounds wherein R and A together form a hexyl group.

Most preferred are those formula 1 compounds wherein $R_1$ is a hydrogen, A is not present, and R is a phenyl, thienyl, p-chlorophenyl, p-fluorophenyl, p-methoxyphenyl, p-methylphenyl, p-hydroxyphenyl, thianaphthylenyl, or cyclopentyl group. Also most preferred are those formula 1 compounds wherein $R_1$ is hydrogen, A is a methylene or ethylene and R is a phenyl group or wherein $R_1$ is hydrogen and R and A together form a n-hexyl group.

Some of the compounds of this invention are known and the preparation of these compounds is described in *Tetrahedron Letters*, 28(20), 2207–2210 (1987). The preparation of those compounds not specifically described in the prior art can readily be prepared using analogous procedures. For example, an aromatic or aliphatic Grignard reagent, R—MgX or R—A—MgX, wherein R and A are as defined for formula 1 and wherein X is chlorine, bromine, or iodine is reacted with 10 mole per cent of copper bromide-dimethyl sulfide or a nickel (0) catalyst such 1,3-bis(diphenyl-phosphinopropane)nickel(II) chloride in anhydrous diethyl ether at from about −60° C. to about 0° C., preferably at about −25° C. followed by the addition of the bis-trimethylsilyl protected 4-methoxy-2-butynyla-mine of the formula 2

$$CH_3OCH_2C\equiv CCH_2N(Si(CH_3)_3)_2 \qquad 2$$

to result in a N,N-bis-trimethylsilylated derivative of formula 3.

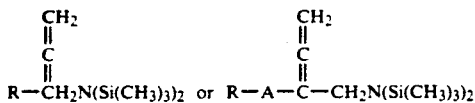

Solvents other than diethyl ether which are suitable are any of those solvents used by those skilled in the art when performing the Grignard reaction such as tetrahydrofuran (THF), or 1,2-dimethoxyethane (DME). Addition of the butynylamine (2) is generally dropwise with stirring. The reaction time varies depending upon the reactivity of the chosen Grignard reagent and can vary from several minutes to several hours, typically from about 10 minutes to about 24 hours. Reaction time also depends upon the temperature of the reaction mixture. While cooling to substantially below 0° C. during the addition of the Grignard reagent is beneficial, allowing the reaction mixture to warm to from about 0° C. to about room temperature (25° C.) facilitates the reaction.

Deprotection of the formula 3 protected silylamines results in the desired allenylamine of formula 1. Deprotection can be accomplished in any manner generally known to those ordinarily skilled in the art. Applicants have successfully deprotected the formula 3 compounds by flash chromatography on, for example, silica gel eluting with a solvent such as chloroform. The resulting eluent upon solvent removal is quantitatively pure.

The preparation of those compounds wherein R is an hydroxy substituted phenyl group are more expeditiously carried out if the hydroxy group is suitably protected. These hydroxy groups can be conveniently protected as their dimethyl-tert-butylsilyl derivatives. Subsequent to the catalyzed Grignard reaction, the silylated hydroxy group can be deprotected in the usual manner such as by treatment with a buffered (pH=7) solution of sodium fluoride, such as a 1M solution of sodium fluoride.

The ability of the compounds of this invention to be useful in the treatment of diseases and conditions associated with defects in collagen metabolism such as occurs in various fibrotic conditions, for example, lung fibrosis, as well as in proliferative vitreo retinopathy, surgical scarring, systemic sclerosis, scleroderma, and keloids can be demonstrated by the ability of the compounds to inhibit lysyl oxidase. The lysyl oxidase inhibition activity for representative members of the compounds of this invention is tabulated in Example 1.

The amount of the active ingredient to be administered can vary widely according to the particular dosage unit employed, the period of treatment, the age and sex of the patient treated and the nature and extent of the disorder treated. The total amount of the active ingredient to be administered will generally range from about 5 mg to about 500 mg per day. A unit dosage may contain from 25 to 500 mg of active ingredient, and can be taken one or more times per day. The active compound of formula 1 can be administered with a pharmaceutical carrier using conventional dosage unit forms either orally, parenterally, or topically. In the case of abnormal collagen deposition of the skin, topical administration to the diseased site is preferred, and in the case of abnormal collagen deposition to internal sites, local administration where possible and practical is preferred. Where local or topical application is not possible, systemic administration should be of short duration lasting, for example, for only a few days, and the patient should be closely monitored for adverse affects.

Coadministration of a compound of formula 1 with penicillamine, a compound known to be useful in the treatment of diseases and conditions characterized by abnormal collagen deposition but known to function by other than the inhibition of lysyl oxidase, is expected to be advantageous. The effective dosage of a compound of formula 1 when co-administered with penicillamine is expected to be less than the effective dosage when administered alone and will depend on the quantity and frequency of penicillamine co-administered. Therapy should be instituted at lower dosages of the formula 1 compound and of penicillamine than would be used in the absence of co-administration and the dosages thereafter altered to achieve the desired effect. The amount of compound of formula 1 as compared to the amount of penicillamine can vary from, for example, 1:1 to 1:500. It is understood that a compound of formula 1 can be administered substantially at the same time as, prior to; or after administration of penicillamine.

For oral administration the compounds can be formulated into solid or liquid preparations such as capsules, pills, tablets, troches, lozenges, melts, powders, solutions, suspensions, or emulsions. The solid unit dosage forms can be a capsule which can be of the ordinary hard- or soft-shelled gelatin type containing, for example, surfactants, lubricants, and inert fillers such as lactose, sucrose, calcium phosphate, and cornstarch. In another embodiment the compounds of this invention can be tableted with conventional tablet bases such as lactose, sucrose, and cornstarch in combination with binders such as acacia, cornstarch, or gelatin, disintegrating agents intended to assist the break-up and dissolution of the tablet following administration such as potato starch, alginic acid, corn starch, and guar gum, lubricants intended to improve the flow of tablet granulations and to prevent the adhesion of tablet material to the surfaces of the tablet dies and punches, for example, talc, stearic acid, or magnesium, calcium, or zinc stearate, dyes, coloring agents, and flavoring agents intended to enhance the aesthetic qualities of the tablets and make them more acceptable to the patient. Suitable excipients for use in oral liquid dosage forms include diluents such as water and alcohols, for example, ethanol, benzyl alcohol, and the polyethylene alcohols, either with or without the addition of a pharmaceutically acceptable surfactant, suspending agent, or emulsifying agent.

The compounds of this invention may also be administered parenterally, that is, subcutaneously, intravenously, intramuscularly, or interperitoneally, as injectable dosages of the compound in a physiologically acceptable diluent with a pharmaceutical carrier which can be a sterile liquid or mixture of liquids such as water, saline, aqueous dextrose and related sugar solutions, an alcohol such as ethanol, isopropanol, or hexadecyl alcohol, glycols such as propylene glycol or polyethylene glycol, glycerol ketals such as 2,2-dimethyl-1,3-dioxolane-4-methanol, ethers such as poly(ethyleneglycol) 400, an oil, a fatty acid, a fatty acid ester or glyceride, or an acetylated fatty acid glyceride with or without the addition of a pharmaceutically acceptable surfactant such as a soap or a detergent, suspending agent such as pectin, carbomers, methylcellulose, hydroxypropylmethylcellulose, or carboxymethylcellulose, or emulsifying agent and other pharmaceutically acceptable adjuvants. Illustrative of oils which can be used in the parenteral formulations of this invention are those of petroleum, animal, vegetable, or synthetic origin, for example, peanut oil, soybean oil, sesame oil, cottonseed oil, corn oil, olive oil, petrolatum, and mineral oil. Suitable fatty acids include oleic acid, stearic acid, and isostearic acid. Suitable fatty acid esters are, for example, ethyl oleate and isopropyl myristate. Suitable soaps include fatty alkali metal, ammonium, and triethanolamine salts and suitable detergents include cationic detergents, for example, dimethyl dialkyl ammonium halides, alkyl pyridinium halides, and alkylamine acetates; anionic detergents, for example, alkyl, aryl, and olefin sulfonates, alkyl, olefin, ether, and monoglyceride sulfates, and sulfosuccinates; nonionic detergents, for example, fatty amine oxides, fatty acid alkanolamides, and polyoxyethylenepolypropylene copolymers; and amphoteric detergents, for example, alkylbeta-aminopropionates, and 2-alkylimidazoline quarternary ammonium salts, as well as mixtures. The parenteral compositions of this invention will typically contain from about 0.5 to about 25% by weight of the active ingredient in solution. Preservatives and buffers may also be used advantageously. In order to minimize or eliminate irritation at the site of injection, such compositions may contain a non-ionic surfactant having a hydrophilelipophile balance (HLB) of from about 12 to about 17. The quantity of surfactant in such formulations ranges from about 5 to about 15% by weight. The surfactant can be a single component having the above HLB or can be a mixture of two or more components having the desired HLB. Illustrative of surfactants used in parenteral formulations are the class of polyethylene sorbitan fatty acid esters, for example, sorbitan monooleate and the high molecular weight adducts of ethylene oxide with a hydrophobic base, formed by the condensation of propylene oxide with propylene glycol.

The compounds of this invention are preferably administered topically when used to treat a disease or condition characterized by abnormal collagen deposition of the skin. Any of the above described liquid formulations, including gels and ointments, may take the form of skin lotions and creams and may also contain emollients, perfumes, astringents, shaving lotions, colognes, cosmetic foundations, and similar preparations. In general a topical composition of this invention will contain from about 0.01 g to about 5 g of a compound of formula 1 per 100 ml of the composition.

The following examples illustrate the activity and formulation of the compounds of this invention.

EXAMPLE 1

Lysyl Oxidase Inhibition Studies

Lysyl oxidase preparation is obtained from bovine aorta by the procedures modified from M. A. Williams and H. M. Kagan, *Anal. Biochem.* 149, 430–437 (1985) and H. M. Kagan and K. A. Sullivan, *Methods in Enzyml.* 82, 637–650 (1982). The aorta is obtained fresh on the day of the enzyme preparation and is maintained at 4° C. for the duration of its use in the experiments. The aorta is ground fine and is homogenized for 90 seconds in buffer (2.5 ml of a buffer consisting of 16 mM potassium phosphate and 1 mM phenylmethylsulfonyl fluoride/g of tissue) with 0.15M NaCl added, then the mixture is centrifuged (20 minutes at 11,000×g). The homogenization followed by centrifugation procedure is repeated with buffer plus 0.15 M NaCl, buffer alone, and buffer plus 1M urea. After homogenization in 1M urea, the mixture is stirred for 1 hour prior to centrifugation. The resulting pellet is homogenized in buffer plus 4M urea, stirred for 18 hours, and centrifuged. The supernatant with lysyl oxidase activity is saved. The tissue is homogenized in buffer plus 4M urea, stirred overnight, and centrifuged twice more. The supernatants with lysyl oxidase activity are saved.

The assay is adopted from that of P. C. Trackman, et al., *Anal. Biochem.* 113, 336–342 (1981). Each assay consists of two tubes, one that contains 0.2 mM β-aminopropionitrile, BAPN, from the start and one to which BAPN is added to quench the reaction. Lysyl oxidase preparation (0.150 ml), urea (0.300 ml, 4M), buffer (0.930 ml, 200 mM borate at pH =8.2), homovanillic acid (0.020 ml of 50 mM solution), and horseradish peroxidase (0.010 ml of Sigma Type II at 5 mg/ml protein) are incubated for 2 minutes at 55° C. in a test tube. Cadaverine (0.100 ml of 150 mM) and test compound, if any, is added and the incubation continued at 55° C. for an additional 10 minutes. The test tubes containing this mixture are then cooled in a ice bath after adding BAPN to any tubes not containing it. The difference in fluorescence (excitation 315 nm and emission 425 nm) between corresponding tubes that received BAPN at 0 minutes and at 10 minutes is a measure of enzyme activity. A standard curve to determine the amount of cadaverine converted by lysyl oxidase is prepared as follows. Assay mixtures containing BAPN are made up as described and known amounts of hydrogen peroxide are added simultaneously with cadaverine and the fluorescence changes after 10 minutes reaction are determined.

Using this method the lysyl oxidase inhibiting activity expressed as $IC_{50}$ (inhibitory concentration), that is the concentration of test compound required to inhibit the enzyme activity by 50 percent, was determined for various compounds of this invention. The results are shown in Table 1.

TABLE 1

LYSYL OXIDASE INHIBITION ACTIVITY
OF ALLENYLAMINES

| TEST COMPOUND | $IC_{50}$ (M) |
| --- | --- |
| β-ethenylidene-1-octanamine hydrochloride | $1 \times 10^{-9}$ |
| β-ethenylidenebenzo[b]thiophene2-ethanamine hydrochloride | $1 \times 10^{-8}$ |
| β-ethenylidene-4-methoxybenzeneethanamine 4-methylbenzenesulfonate | $1 \times 10^{-8}$ |
| β-ethenylidene-2-thiopheneethanamine | $1 \times 10^{-8}$ |

TABLE 1-continued
LYSYL OXIDASE INHIBITION ACTIVITY OF ALLENYLAMINES

| TEST COMPOUND | IC$_{50}$ (M) |
|---|---|
| 4-methylbenzenesulfonate β-ethenylidenebenzene-1-pentanamine hydrochloride | 1 × 10$^{-9}$ |
| β-ethenylidenebenzene-1-butanamine hydrochloride | 1 × 10$^{-9}$ |

EXAMPLE 2

β-Ethenylidene-2-Thiopheneethanamine-4-Methylbenzenesulfonate

Under N$_2$, 170 mg (3 mole %) 1,3-bis(diphenylphosphinopropane)nickel (II) chloride (NiCl$_2$(dppp)) is added to 30 ml dry Et$_2$O. The bis-trimethylsilyl protected 4-methoxy-2butynylamine (2.47 g, 10.2 mmol) is added via syringe and then 7 ml (21 mmol) 2M 2-thienylmagnesium bromide. The reaction exotherms mildly. After 20 hours, the reaction is complete by GC analysis. The silylated product is isolated by shaking with dilute NH$_4$OH and extracting into EtOAc (3×120 ml). After drying (K$_2$CO$_3$) and concentration, 2.68 g crude product is obtained. Purification and desilylation by flash chromatography (300 g silica gel, elute with CHCl$_3$ then CHCl$_3$:MeOH:conc. NH$_4$OH (100:10:1) gives 1.22 g (87%) as a light tan oil after drying under high vacuum. The tosylate salt is prepared by adding one equivalent of an ethanolic solution of the acid to an Et$_2$O solution of the free base and isolated as a white solid; mp. 126°-127° C. (isopropanol).

IR (KBr) 1960, 1933, 840 cm$^{-1}$.
$^1$-NMR (ME$_2$SO-d$_6$) δ8.15 (br s, 3), 7.47–7.52 (M,3), 7.06–7.15 (m,4), 5.53–5.55 (t, 2,J-3.2), 3.87 (br s,2), 2.29 (s,3).
MS (CI) m/z 173 (tosyl acid), 152 (MH$^+$), 135 (MH$^+$—NH$_3$), 123 (MH$^+$—CH=NH).
Anal Calcd for C$_8$H$_9$NS: C, 55.71; H, 5.30; N, 4.33. Found: C, 55.75; H, 5.44; N, 4.28.

EXAMPLE 3

β-Ethylenylidene-Benzo[β]Thiophene-2-Ethanamine Hydrochloride

2-Thianaphthylmagnesium bromide is prepared from 2-thianaphthyllithium and MgBr$_2$.OEt$_2$. Using a procedure similar to that of Example 2, 3.85 g crude silylate product is isolated. Usual flash chromatography workup results in an unidentified, insoluble purple solid. The desired product is isolated by adding 1M ethanolic HCl (95% of theoretical) to an ethereal solution of the free base. The product is a pale yellow solid (1.7 g, 72%); mp 235° C. (dec) (EtOH).

MS (EI@70eV) m/z 201 (M$^+$), 200 (M$^+$—H), 184 (M$^+$—NH3), 172 (M$^+$—CH=NH).
Anal Calcd for C$_{12}$H$_{11}$NS.HCl:C, 60.63; H, 5.09; N, 5.89. Found: C, 60.86; H, 5.21; N, 5.65.

EXAMPLE 4

β-Ethenylidene-4-Fluorobenzeneethanamine-4-Methylbenzenesulfonate

To a mixture of dry ether (30 ml) and CuBr.Me$_2$S (2.05 g 10.0 mmol) cooled to −30° C. under nitrogen atmosphere was added 4-fluorophenylmagnesium bromide (10 ml of a 2M solution in diethylether, 20 mmol) dropwise. The reaction temperature was kept below −20° C. during the addition and was then stirred at −25° C. for 15 min. The yellow-brown slurry was treated with bis-trimethylsilyl protected 4-methoxy-2-butynylamine (1.86 g, 7.65 mmol) and the reaction allowed to warm to room temperature. The reaction was monitored by GC and was complete after 18 hours. The dark slurry was poured onto 10% NH$_4$OH (100 ml) and diluted with EtOAc (50 ml). The blue aqueous layer was washed with EtOAc (2×75 ml), the combined organic layers washed with brine (100 ml) and dried (Na$_2$SO$_4$). The solvent was removed in vacuo yielding a yellow oil, (2.2 g) which was hydrolyzed to desired product by flash chromatography on silica gel (500 ml, 23×7 cm) using CHCl$_3$ as the initial solvent to remove biphenyl impurity and then eluting the bis-trimethylsilyl reactant with 100:10:1/CHCl$_3$:MeOH:NH$_4$OH. The product was obtained as a yellow oil (1.07 g, 85.7%). The oil was dissolved in dry ether (50 ml) and treated with a solution of oxalic acid (0.59 g, 6.56 mmol) in absolute ethanol (5 ml). The resulting white solid was collected on a sintered glass funnel and washed with ether (1.32 g): mp 152°–153° C. (Insert at 150° C). A sample was recrystallized from isopropyl alcohol/water (3:1) to give analytically pure sample: mp 192°–193° C. (Insert at 185° C).

IR(KBr) 1950, 884 cm$^{-1}$.
$^1$-NMR ((CH$_3$)$_2$SO-d$_6$) δ7.42 (2H, m, J=8.73), 7.32 (4H, m), 5.40 (2H, t, J=2.90), 3.77 (2H, t, J=2.90).
Mass Spectrum (EI@70 eV), m/e 163 (M$^+$), 162 (M$^+$—H), 146 (M$^+$—NH$_3$), 133 (M$^+$—CH$_2$=NH).
Anal Calcd for C$_{12}$H$_{12}$FNO$_4$:C, 63.45; H, 5.33; N, 6.73. Found: C, 63.29; H, 5.28; N, 6.62.
Tosylate Salt: mp 164°–166° C. (CH$_3$CN).

EXAMPLE 5

β-Ethenylidene-4-Chloro-Benzeneethanamine-4-Methylbenzenesulfonate

Prepared in a similar manner to Example 4 to provide the free base as a tan oil (1.77 g, 88.5%).
Tosylate 82% conversion from free base, mp 159°–160.5° C. (isopropanol).
IR(KBr) 1940, 860 cm$^{-1}$.
$^1$H-NMR (Me$_2$SO-d$_6$) δ8.08(hr s, 3) 7.39–7.49 (m,7), 7.10–7.12 (d,2), 5.54–5.56 (t, 2, J=3.26), 3.89–3.91 (t,2, J=3.26), 2.29 (s,3).
Mass Spec. (CI) m/z 180(MH$^+$), 173 (tosyl acid).
Anal. Calcd for C$_{10}$H$_{10}$ClN. C$_7$H$_8$O$_3$S; C, 58.0; H, 5.16; N, 3.98. Found: C, 57.6; H, 5.16; N, 3.79.

EXAMPLE 6

β-Ethenylidene-4-Methylbenzeneethanamine-4-Methylbenzenesulfonate

Prepared in a similar manner as in Example 5 using 10 mole % CuBr.Me$_2$S to provide the product as a yellow oil (1.67 g, 98.0%) which was then converted to the oxalate salt as described previously (1.88 g). The oxalate salt (1.0 g) was treated with 2N NaOH (20 ml), extracted with ether (2×15 ml), dried (Na$_2$SO$_4$), and filtered. The filtrate was treated with p-toluenesulfonic acid (3.8 ml of a 1M solution in ethanol). The solvent was removed in vacuo yielding a yellow oil (0.9 g) which crystallized upon addition of ether. A sample was recrystallized from CH$_3$CN to give analytically pure product: mp 134°–136° C.

IR (KBr) 1940, 813 cm$^{-1}$.
$^1$H-NMR ((CH$_3$)$_2$SO-d$_6$) δ8.09 (3H, br s), 7.48 (2H, d, J=8.17, TsOH), 7.28 (2H, d, J=8.36), 7.22 (2H, d,

J=8.36), 7.12 (2H, d, J=8.17, TsOH), 5.50 (2H, t, J=2.68), 3.88 (2H, t, J=2.68), 2.31 (3H, s), 2.29 (3H, s, TsOH)

Mass Spectrum (EI at 70 eV), m/e 172 (TsOH), 159 (M+), 158 (M+—H), 144 (M+—CH$_3$), 130(M+—CH$_2$=NH).

A small sample of the oxalate salt was dissolved in water and placed on a column of Dowex 1-x2( (Cl-form) and eluted with water. UV absorbing fractions were combined and lypholized to a white powder, mp 205°-207° C. (dec). Anal. Calcd for C$_{11}$H$_{14}$ClN .1/8 H$_2$O: C, 66.75; H, 7.26; N, 7.08. Found: C, 66.81; H, 7.29; N, 6.91.

EXAMPLE 7

β-Ethenylidene-4-Methoxybenzeneethanamine-4-Methylbenzenesulfonate

Prepared in a similar manner as in Example 5 using 10 mole % CuBr.Me$_2$S to provide the product as a yellow oil (1.74 g, 95.5%) which was then converted to the oxalate salt as described previously (1.52 g). The tosylate salt was prepared in a similar manner to provide an off-white solid. A sample was recrystallized from CH$_3$CN to give analytically pure product: mp 166°-168° C. (Insert at 160° C).

IR(KBr) 1943, 820, 830 cm$^{-1}$.

$^1$H-NMR ((CH$_3$)$_2$SO-d$_6$) δ8.02 (3H, br s), 7.48 (2H, d, J=8.58, TsOH), 7.31 (2H, d, J=8.19), 7.12 (2H, d, J=8.19), 6.98 (2H, d, J=8.58, TsOH), 5.48 (2H, t, J=3.39), 3.87 (2H, t, J=3.39), 3.76 (2H, s), 2.29 (3H, s, TsOH)

Mass Spectrum (EI at 70 eV), m/e 172 (TsOH), 175 (M+), 174 M+—H), 160 (M+—CH$_3$), 144 (M+—OCH$_3$), 146 (M+—CH$_2$=NH).

Anal Calcd for C$_{18}$H$_{21}$NO$_4$S: C, 62.23; H, 6.09; N, 4.03. Found: C, 62.15; H, 6.13; N, 4.04.

EXAMPLE 8

β-Ethenylidene-1-Octanamine Hydrochloride

Procedure A. Prepared in a similar manner as Example 5 using 10 mole % CuBr.Me$_2$S to provide TMS compound as a clear oil (2.5 g). This crude product (2.4 g, 8.06 mmol) was dissolved in ether (30 ml) and treated with EtOH/HCl (10 ml of a 12M solution). The solution was allowed to stand briefly, the solvent removed in vacuo yielding a light yellow oil which crystallized upon cooling. The solid was slurried with ether (20 ml) and collected on a sintered glass funnel (1.26 g, 82.4%). A sample was recrystallized from CH$_3$CN to give analytically pure product: mp 120°-121° C. (softens at 102° C.). IR(KBr) 1968, 880, 895 cm$^{-1}$.

$^1$HNMR ((CH$_3$)$_2$SO-d$_6$) δ8.30 (3H, br s), 4.97 (2H).

Procedure B. Prepared in a similar manner as Example 2, but cooling to 10° C. prior to addition of 2, to provide crude product (2.19 g). This crude product (2.19 g) is converted to its HCl salt in a similar manner as Procedure A to give crude product (1.0 g, 52.3%) as a brown solid. A sample was recrystallized from CH$_3$CN to give analytically pure product: mp 120°-121° C. (softens at 88° C).

EXAMPLE 9

β-Ethenylidenecyclopentaneethanamine Hydrochloride

Prepared in a similar manner as Example 2 using 10 mole % CuBr.Me$_2$S to provide crude product as a yellow oil (3.04 g). The crude TMS compound was converted to the HCl salt in a similar manner as above. (1.74 g, 51.2%). A sample was recrystallized from CH$_3$CN to provide analytically pure product: mp 113°-115° C. (Insert at 113° C).

IR(KBr) 1960, 878 cm$^{-1}$.

$^1$H-NMR ((CH$_3$)$_2$SO-d$_6$) δ8.31 (3H, br s), 5.03 (2H, m, J-0.01 Hz), 3.62 (2H, m, J=0.01 Hz), 2.45 (1H, m, J-0.01 Hz), 1.87-1.29 (8H, m).

Mass Spectrum (EI@70 eV), m/e 137 (M+), 136 (M+—H), 122 (M+—CH$_3$), 108 (M+—CH$_2$=NH).

EXAMPLE 10

β-Ethylenylidene-4-Hydroxybenzeneethanamine 4-(t-Butyldimethylsilyloxy)-1-bromobenzene was placed in an oven-dried, 100 ml, 3-necked round bottom flask equipped with a stir bar, thermometer, rubber septum and glass stopper along with 30 ml ether. This mixture was cooled to 0° C. and n-BuLi added via syringe. This was stirred for 30 min, a small aliquot removed, quenched with solid NaHCO$_3$.

When GC indicates that no starting material remains, MgBr$_2$.Et$_2$O was added as a solid and the reaction stirred for 15 minutes.

In another oven-dry, 100 ml, 3-necked flask was placed a stirrer bar, thermometer, rubber septum and glass stopper CuBr.Me$_2$S in 30 ml ether was added and this cooled to —35° C. before the above Grignard reagent was added, followed by bis-trimethylsilyl protected 4-methoxy-2-butynylamine (2). The ice-bath was removed and the reaction allowed to stir at room temperature. After stirring overnight the reaction was quenched with dilute NH$_4$OH, extracted into EtOAc. Organics washed with brine, dried over Na$_2$SO$_4$ and conc. under reduced pressure to give 3.31 g of crude bis-silylated product.

Flash chromatography (CHCl$_3$ the CHCL$_3$:MeOH:NH$_4$OH/100:10:1) gave 1.56 g of the t-butyldimethylsilyloxyhydroxy protected allene as a yellow oil (85.8%).

The reagents were stirred vigorously under N$_2$-atmosphere and the white precipitate was filtered and air dried (0.73 g). Recrystallization (IPA) gave 190 mg of product as white crystals, mp 180°-183° C. 2nd crop, 110 mg mp 180°-181° C.

EXAMPLE 11

β-Ethenylidenebenzenebutanamine Hydrochloride

Prepared in a similar manner as Example 5 (Grignard reagent prepared from (3-bromoethyl)benzene and magnesium in ether) using 10 mole % CuBr.Me$_2$S to provide the product as an oil after flash chromatography. The oil was dissolved in ether and treated with ether and HCl to provide a white solid (0.52 g); mp 202-°204° C. (i-PrOH).

Anal. Calcd for C$_{12}$H$_{15}$N.HCl: C, 68.72; H, 7.69; N, 6.68 Found: C, 68.76; H, 7.91; N, 6.59

EXAMPLE 12

β-Ethenylidenebenzenepentanamine Hydrochloride

Prepared in a similar manner as Example 5 (Grignard reagent prepared from 1-bromo-3-phenylpropane and magnesium in ether) using 10 mole % CuBr.Me$_2$S to provide product as an oil after flash chromatography. The oil was dissolved in ether and treated with ether and HCl. The crystals were allowed to digest for 1 hour in refluxed ether and collected by filtration (1.2 g) mp 88°-91° C. (CH$_3$CN).

Anal. Calcd for C$_{13}$H$_{17}$N.HCl.0.1H$_2$O: C, 69.54; H, 8.17; N, 6.24. Found: C, 69.71; H, 8.21; N, 6.13

We claim:

1. A method of treating diseases and conditions associated with the abnormal deposition of collagen in a patient in need thereof which comprises administering to the patient a lysyl oxidase inhibiting amount of penicillamine together with an effective amount of ac compound of the formula

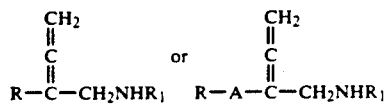

wherein
R$_1$ is a hydrogen, or a (C$_1$-C$_4$)alkyl group;
A is a divalent radical group selected from

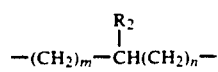

wherein
R$_2$ is hydrogen, methyl, or ethyl, and m and n, independently, are an integer from 0 to 16, provided that m+n cannot be greater than 17;

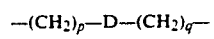

wherein
D is oxygen or sulfur, p is an integer of from 0 to 16, and q is an integer of from 1 to 16, provided that m+n cannot be greater than 17; and

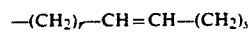

wherein
s is an integer of from 1 to 16 and r is an integer of from 0 to 16, provided that r+s cannot be greater than 16; and
R is a methyl group, a (C$_3$-C$_8$)cycloalkyl group, a phenyl, or a phenyl substituted with one or two members of the group (C$_1$-C$_5$)alkyl, (C$_1$-C$_5$)alkoxy, hydroxy, chloro, bromo, fluoro, iodo, trifluoromethyl, nitro, (C$_1$-C$_5$)alkylcarbonyl, benzoyl, or phenyl; or wherein A is a divalent radical group selected from

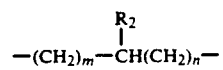

wherein
m, n and R$_2$ are as defined above, then R can additionally be a —NH$_2$ group;
or a pharmaceutically acceptable salt thereof.

2. A method of claim 1 which comprises administering to the patient a lysyl oxidase inhibiting amount of penicillamine together with an effective amount of β-ethenylidene-4-methylbenzeneethanamine or a pharmaceutically acceptable salt thereof.

* * * * *